(12) United States Patent
Molz et al.

(10) Patent No.: US 7,440,548 B2
(45) Date of Patent: *Oct. 21, 2008

(54) X-RAY DEVICE WITH AN X-RAY SOURCE FIXED TO A CEILING STAND

(75) Inventors: Claudius Molz, Buckenhof (DE); Peter Scheuering, Fürth (DE)

(73) Assignee: Siemens Aktiengesellschaft, Munich (DE)

( * ) Notice: Subject to any disclaimer, the term of this patent is extended or adjusted under 35 U.S.C. 154(b) by 60 days.

This patent is subject to a terminal disclaimer.

(21) Appl. No.: 11/453,612

(22) Filed: Jun. 15, 2006

(65) Prior Publication Data

US 2006/0285643 A1    Dec. 21, 2006

(30) Foreign Application Priority Data

Jun. 15, 2005   (DE) .................. 10 2005 027 672

(51) Int. Cl.
*H05G 1/10* (2006.01)

(52) U.S. Cl. ........................ 378/101; 378/197
(58) Field of Classification Search ................ 378/101, 378/111, 112, 193–197
See application file for complete search history.

(56) References Cited

U.S. PATENT DOCUMENTS

| 6,215,846 B1* | 4/2001 | Mazess et al. ............ 378/62 |
| 2005/0031087 A1* | 2/2005 | Maschke ................. 378/196 |
| 2006/0262906 A1 | 11/2006 | Molz et al. | |

FOREIGN PATENT DOCUMENTS

DE    102005022343 A1    11/2006

* cited by examiner

*Primary Examiner*—Courtney Thomas

(57) ABSTRACT

The invention relates to an x-ray device with an x-ray source fixed to a ceiling stand and a generator connected therewith in order to supply voltage. In order to achieve as compact an arrangement as possible, it is proposed in accordance with the invention to provide the generator with means of suspended fixing on a ceiling.

11 Claims, 4 Drawing Sheets

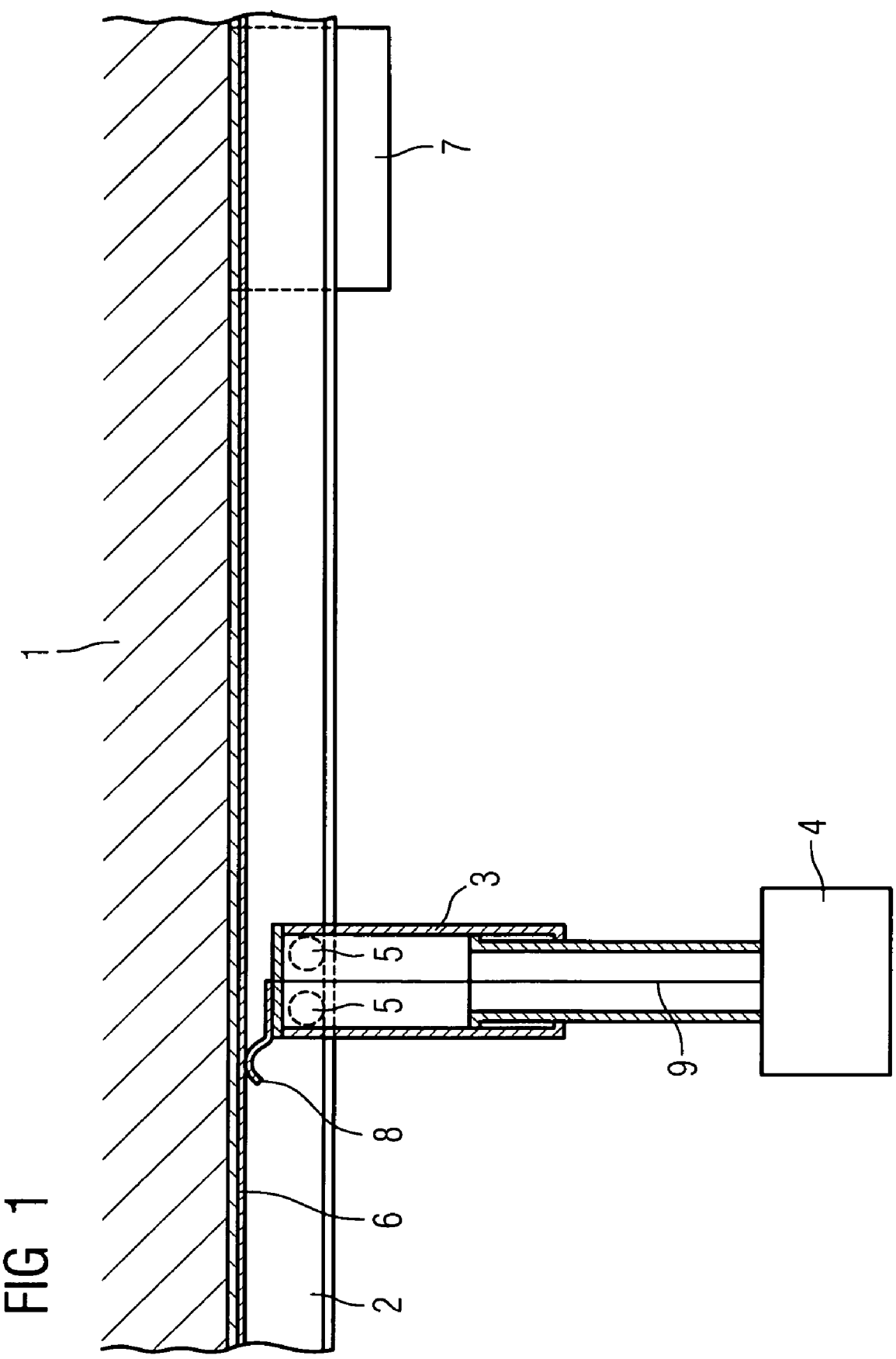

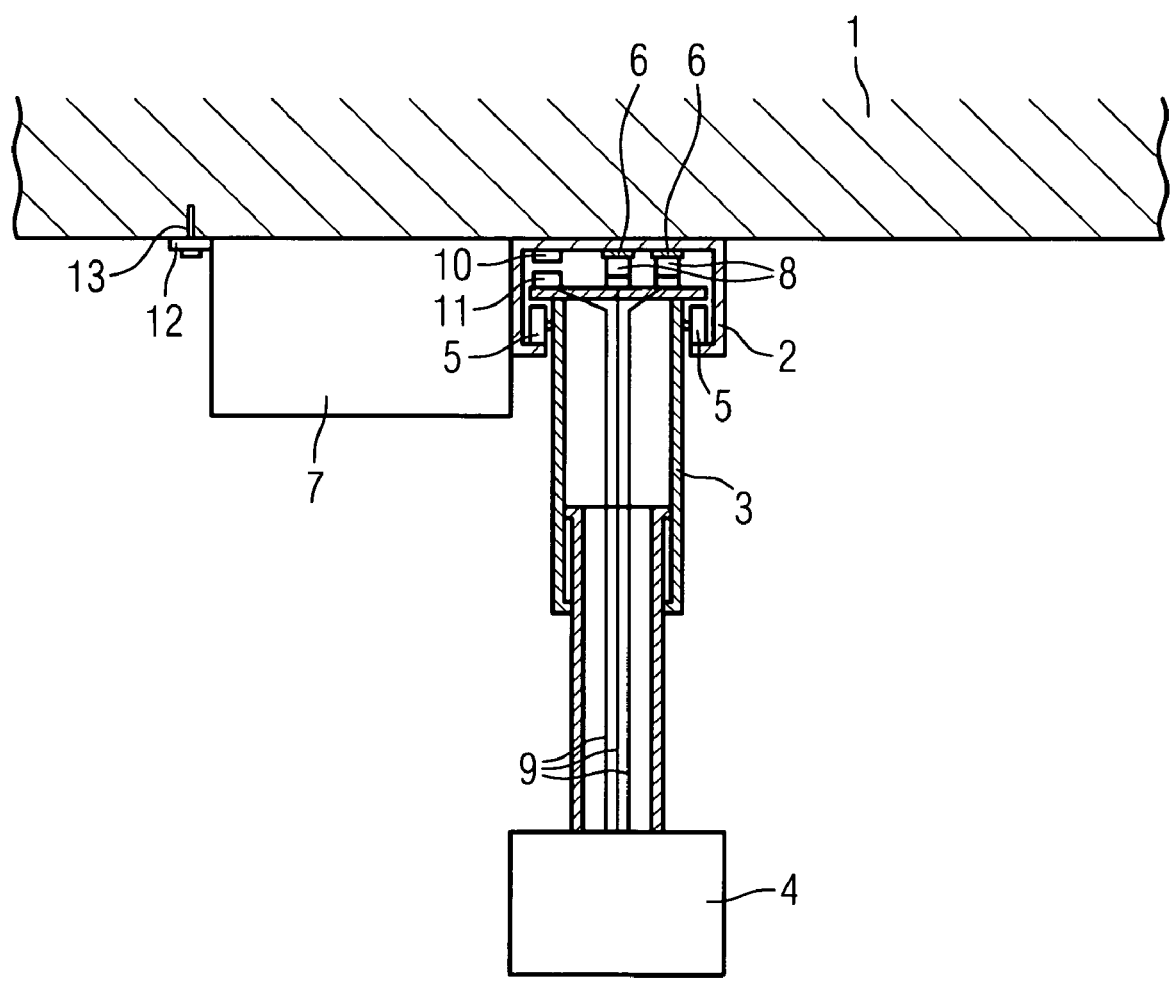

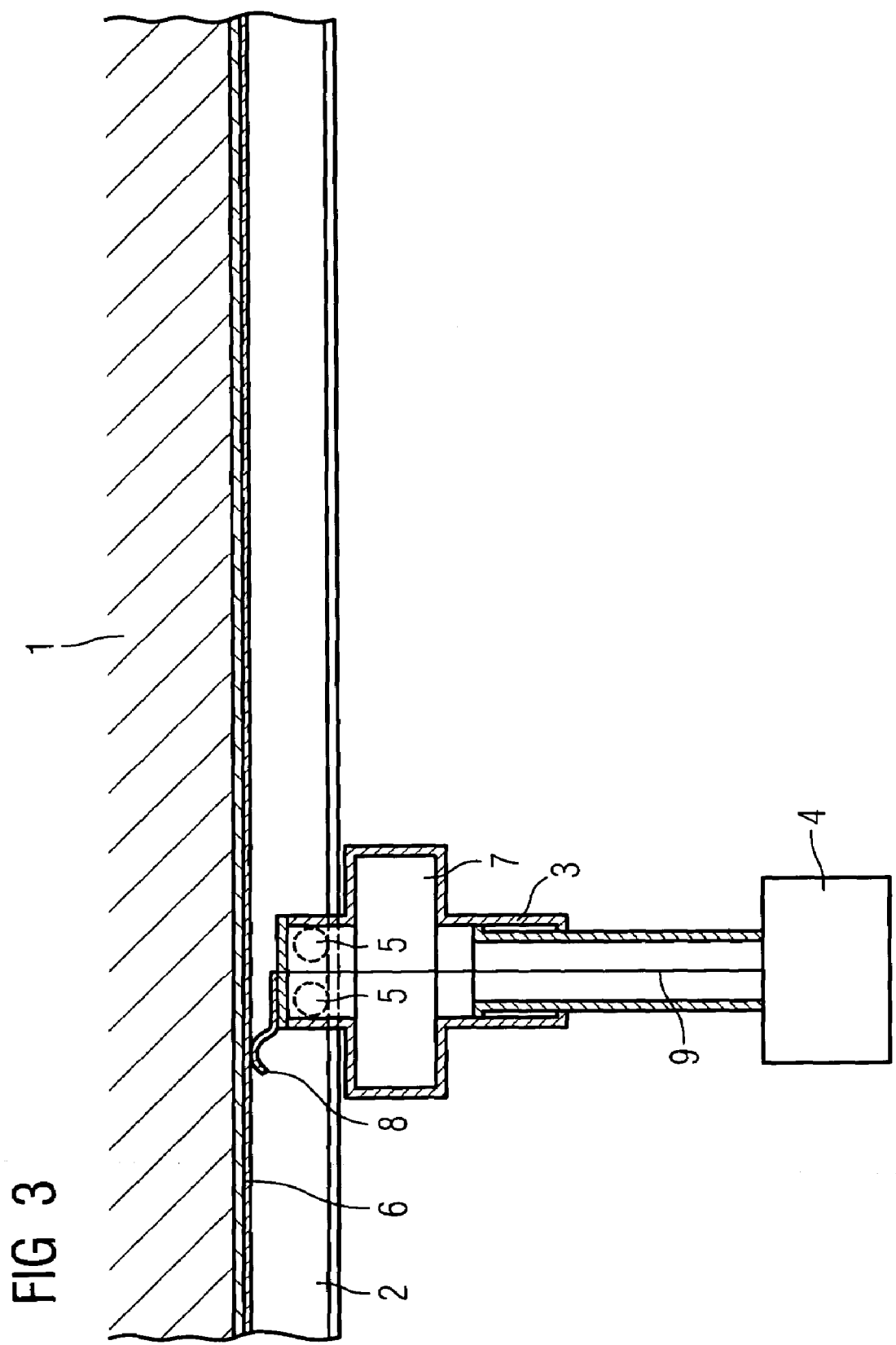

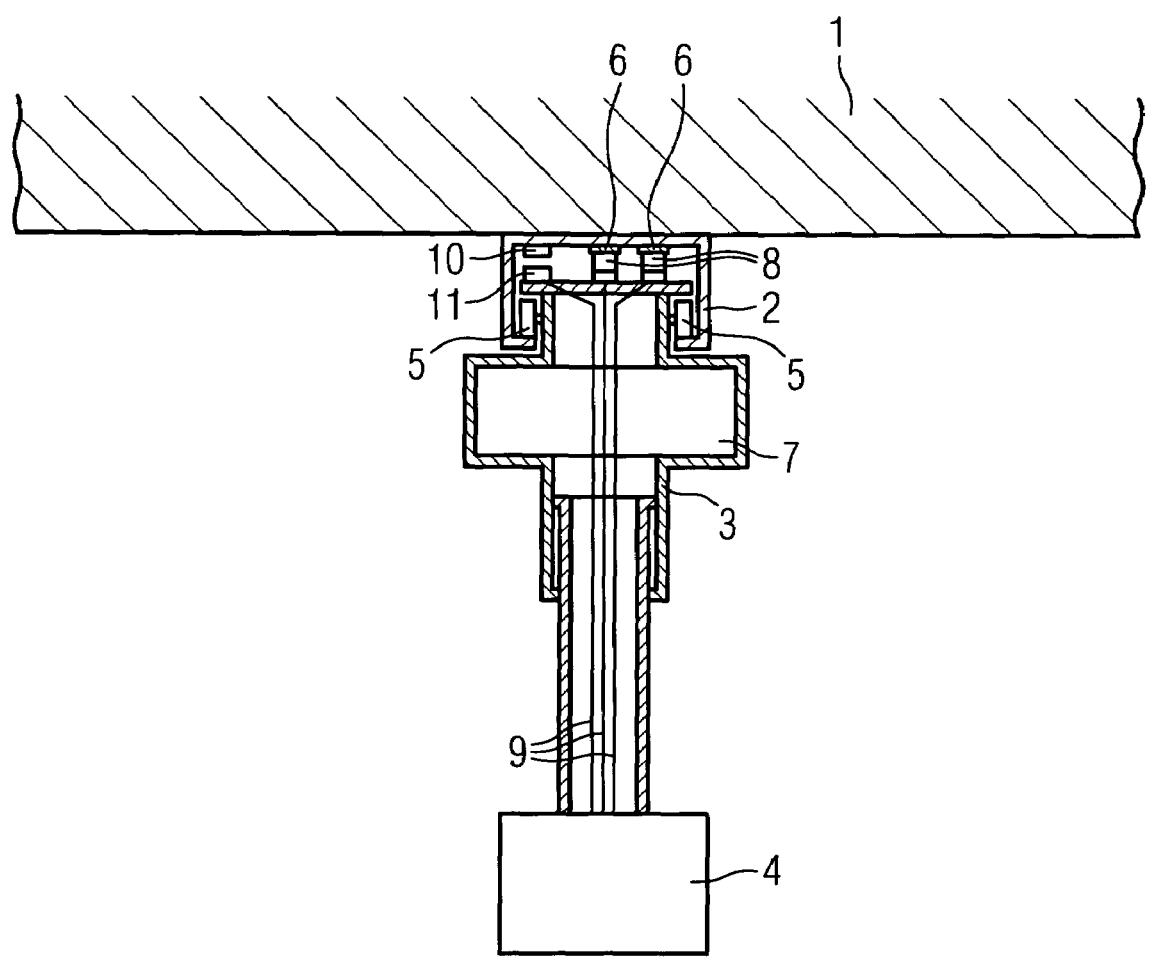

X-RAY DEVICE WITH AN X-RAY SOURCE FIXED TO A CEILING STAND

CROSS REFERENCE TO RELATED APPLICATIONS

This application claims priority of German application No. 10 2005 027 672.5 filed Jun. 15, 2005, which is incorporated by reference herein in its entirety.

FIELD OF THE INVENTION

The invention relates to an x-ray device. The invention further relates to an x-ray device with an x-ray source fixed to a ceiling stand and a generator connected therewith for supplying voltage.

BACKGROUND OF THE INVENTION

Such an x-ray device is widely known according to the prior art. In such devices, a generator for generating high-voltage is positioned or mounted on the floor of a room accommodating the x-ray device. An x-ray source is fixed to a ceiling stand which is accommodated, for its part, in a moveable fashion in a guide rail mounted on the ceiling of the room. The x-ray source is connected to the generator via an up to 24 m long high-voltage cable. The high-voltage cable is fixed to the ceiling via a number of fixing means guided on the guide rail in a moveable fashion and is suspended between the fixing means in loops. If the position of the x-ray source changes, the high-voltage cable can thus be moved to and fro thereby ensuring an adequate freedom of movement of the x-ray tube.

The conventional x-ray device is disadvantageous in many respects, and the high-voltage cable suspended from the ceiling in loops can sometimes interfere with a positioning of the x-ray source. Aside from this, an injudicious movement of the x-ray tube can also lead to patients or staff sustaining injuries. The provision of the relatively stiff high-voltage cable renders the x-ray source moveable only with a relatively significant amount of effort. The assembly of the high-voltage cable is complex and expensive. Finally, the conventional relatively long high-voltage cable has a capacitance which cannot be ignored, which results in an unwanted current flow and thus x-rays even after the generator has been switched off. This in turn undesirably increases the applied dose.

SUMMARY OF THE INVENTION

The object of the invention is to eliminate the disadvantages according to the prior art. In particular, an x-ray device is to be specified which can apply a lowest possible dose. According to a further aim of the invention, the x-ray device is to be as compact as possible and is to operate with a reduced risk of injury.

This object is achieved by the features of the independent claim. Expedient embodiments are set down in the features of the dependent claims.

Provision is made in accordance with the invention for the generator to have a means of suspended fixing to a ceiling. This enables assembly of the generator on the ceiling in the vicinity of the x-ray source. The length of a supply cable or similar can thus be significantly shortened. The unwanted capacitive effects caused by the considerable length of the supply cable according to the prior art can be avoided. The proposed x-ray device enables a particularly precise dose to be applied. The assembly of the generator on the ceiling allows a particularly compact configuration of the x-ray device.

According to an advantageous embodiment the means for suspended fixing can be affixed to a housing. This may consist of bars fixed at an angle at a distance from the housing, which each include a borehole for passing through a screw. However the means of suspended fixing can also comprise a mounting plate, for example, which is mounted on the ceiling. The mounting plate can be designed so that the generator can be suspended from it or inserted into guide rails provided on the mounting plate.

A further embodiment provides for the generator to be accommodated in the housing. According to a further particularly advantageous embodiment, the housing is an integral part of the ceiling stand. The proposed embodiment is of a particularly compact design, which enables the assembly of the x-ray device to be simplified. In particular, the need to separately fix the generator to the ceiling is dispensed with. Aside from that, only the supply voltage for the generator must be supplied in this case. A conductor guiding the high voltage to be provided for supplying the x-ray source can be designed to be particularly short.

A further embodiment provides for the housing to be fixed to the ceiling and the guide rail to extend from the housing. In this case a ceiling stand may be used which is almost unchanged as compared to the prior art. The ceiling stand is relatively light and therefore easily moveable.

According to a further advantageous embodiment, at least one conductor rail is provided on the guide rail, and at least one sliding contact interacting with the conductor rail is provided on the ceiling stand so as to produce an electrical connection with the x-ray source. The conductor rail and the sliding contact interacting therewith allow the conventional long high-voltage cable provided for producing an electrical connection between the generator and the x-ray tube to be dispensed with. At the same time, the great force caused by a movement of the x-ray tube by means of the to-ing and fro-ing of the high-voltage cable is obviated. An x-ray source accommodated in a moveable fashion on a ceiling stand according to the present invention is sufficiently easily moveable that additional motorized equipment to move the x-ray source can be dispensed with. Finally the risk of injury caused by the to-ing and fro-ing of a high-voltage cable is avoided. The conductor rail can be designed to be comparatively significantly shorter than the conventional high-voltage cable so as to ensure an adequate freedom of movement of the x-ray tube.

Consequently, it is possible to apply exactly the desired dose. Finally, the provision of a conductor rail and a sliding contact interacting therewith enables the x-ray device to be assembled in a simpler manner.

Provided that the generator is fixed to the ceiling stand, it is possible to transport only the voltage required to supply the generator via the conductor rail. In this case the conductor rail and the sliding contacts can be particularly simple in design. Finally, in this case a high-voltage connection from the generator to the x-ray source is particularly short, thereby minimizing capacitative effects.

The guide rail can naturally also comprise a number of conductor rails and a number of sliding contacts interacting therewith. In this case, the conductor rails are expediently insulated from one another by an electrically non-conductive material. By way of example, conductor rails arranged next to one another can be separated from one another by a bar made of plastic. In particular, the at least one conductor rail can be accommodated within the guide rail. The sliding contacts are fixed such that short circuits are avoided. The sliding contacts and the conductor rails are enclosed by a housing-type structure such that contact by operating personnel during the operation of the x-ray device is impossible.

The proposed combination of a conductor rail and a sliding contact is expediently designed such that it is possible to supply the x-ray tube with currents in the low-voltage, medium-voltage or high-voltage range.

BRIEF DESCRIPTION OF THE DRAWINGS

An exemplary embodiment of the invention is described in more detail below with reference to the drawings, in which;

FIG. 1 shows a first schematic sectional view of a first embodiment,

FIG. 2 shows a second schematic sectional view according to FIG. 1,

FIG. 3 shows a first schematic sectional view of a second embodiment and

FIG. 4 shows a second schematic sectional view according to FIG. 3.

DETAILED DESCRIPTION OF THE INVENTION

With the x-ray device shown in FIGS. 1 and 2, a guide rail 2 is fixed to a ceiling 1, along which guide rail a ceiling stand 2 can be moved which is preferably designed to be telescopable. An x-ray source 4, shown here schematically, is fixed to the end of the ceiling stand 3. The guide rail 2 can be designed according to a type of U-profile, with further U-profiles pointing inwards being fixed in turn to the two sides of the U-profile, said further U-profiles serving as tracks for rollers 5 fixed to the ceiling stand 3. Two conductor rails 6, which are connected to a generator 7 in an electrically conductive manner, are fixed to a base plate of the U-profile between the sides of the guide rail 3, preferably interconnecting with an electrically insulating layer (not shown here). Sliding contacts 8 are provided on the ceiling stand 3 corresponding to the conductor rails 6, said sliding contacts 8 being pushed against the conductor rails 6 using a spring-biased force. The sliding contacts 8 are connected to the x-ray source 4 in an electrically conductive manner via a cable 9 for instance. Besides the conductor rails 6, a first transceiver 10 for the wireless transmission of data is further provided on the guide rail 3. A second transceiver 11 corresponding therewith is fixed to the ceiling stand 3 such that a data transmission between the first 10 and the second transceiver 11 is possible.

As is particularly apparent from FIG. 2, a housing that surrounds the generator 7 is fitted with a bar 12 fixed at an angle at a distance from the housing, through which a screw 13 is guided in order to fix the housing to the ceiling 1. On the opposite side the housing of the generator 7 can be fixed, for example to the guide rail 2, particularly by means of screws or by using hooks. It is of course also possible to fix the generator 7 to the ceiling 1 in other ways. For example a mounting plate may also be fixed to the ceiling 1 comprising protrusions, recesses or guide lines for example, which interact with the corresponding means provided on the generator 7 in such a way that the generator 7 is suspended on the mounting plate or can be inserted into the mounting plate.

FIGS. 3 and 4 show a second embodiment of the invention. The generator 7 is accommodated here in a ceiling stand 3. To this end, the ceiling stand 3 features a correspondingly suitably designed stand housing in the vicinity of the guide rail 2, which enables the generator 7 to be accommodated. In this case, the generator 7 must only be supplied with a supply voltage required to operate the generator 7 via the conductor rails 6. A high voltage connection from the generator 7 to the x-ray source 5 can be shortened again using this embodiment.

The rollers 5 which are carried in the guide rail 2 serve here as a means of fixing the generator 7 to the ceiling 1.

The invention claimed is:

1. An X-ray device, comprising:
   an x-ray source that is fixed to a ceiling stand; and
   a generator electrically connected with the x-ray source via a sliding contact on the ceiling stand for supplying voltage to the x-ray source that is configured with a suspended fixing to a ceiling in a vicinity of the x-ray source.

2. The X-ray device as claimed in claim 1, wherein the generator is suspended on a mounting plate or inserted into the mounting plate that is mounted on the ceiling.

3. The X-ray device as claimed in claim 1, wherein the generator is accommodated in a housing that is fixed to the ceiling.

4. The X-ray device as claimed in claim 3, wherein the housing is an integral part of the ceiling stand.

5. The X-ray device as claimed in claim 3, wherein the housing is fixed to the ceiling and extended from a guide rail that is fixed to the ceiling for moving the ceiling stand.

6. The X-ray device as claimed in claim 1, wherein the generator is electrically connected with the x-ray source via a cable.

7. The X-ray device as claimed in claim 1, wherein the sliding contact is interacted with a conductor rail provided on a guide rail.

8. The X-ray device as claimed in claim 7, wherein the sliding contact and the conductor rail are enclosed by a housing-type structure.

9. An X-ray device, comprising:
   an x-ray source that is fixed to a ceiling stand;
   a generator electrically connected with the x-ray source for supplying voltage to the x-ray source that is configured with a suspended fixing to a ceiling in a vicinity of the x-ray source;
   a first transceiver provided on a guide rail; and
   a second transceiver interacting with the first transceiver provided on the ceiling stand, the first and second transceivers operatively associated for wireless data transmission between the first and second transceivers.

10. The X-ray device as claimed in claim 9, wherein the first and the second transceivers are optic or radio communication transceivers.

11. A method for an X-ray device, comprising:
   fixing an x-ray source to a ceiling stand that is moveable along a guide rail;
   fixing a generator arranged within a housing to a ceiling in a vicinity of the x-ray source; and
   electrically connecting the generator with the x-ray source for supplying voltage to the x-ray source.

* * * * *